United States Patent [19]

Faust et al.

[11] Patent Number: 4,822,597

[45] Date of Patent: Apr. 18, 1989

[54] ANESTHETIC-CONTAINING CHEWING GUM COMPOSITIONS

[75] Inventors: Steven M. Faust, Stanhope; Subraman R. Cherukuri, Towaco, both of N.J.

[73] Assignee: Warner-Lambert Company, Morris Plains, N.J.

[21] Appl. No.: 72,304

[22] Filed: Jul. 13, 1987

[51] Int. Cl.$^4$ .......................... A61K 9/68; A23G 3/30
[52] U.S. Cl. .................................... 424/48; 424/439; 424/440; 426/3; 426/5
[58] Field of Search ................. 424/48, 439, 440; 426/3, 5

[56] References Cited

U.S. PATENT DOCUMENTS

| | | | |
|---|---|---|---|
| 2,262,087 | 11/1941 | Bartlet et al. | 424/440 |
| 3,011,949 | 12/1961 | Bilotti | 424/48 |
| 4,230,687 | 10/1980 | Sair et al. | 426/534 |
| 4,238,475 | 12/1980 | Witzel et al. | 424/48 |
| 4,610,871 | 9/1986 | Lynch | 424/49 |
| 4,610,872 | 9/1986 | Lynch | 424/49 |

*Primary Examiner*—Ellis P. Robinson
*Assistant Examiner*—P. J. Ryan
*Attorney, Agent, or Firm*—Daniel A. Scola, Jr.; Sandra Gusciora Field

[57] ABSTRACT

This invention relates to chewing gum compositions containing local anesthetics. These compositions readily release the anesthetic such that it is available to anesthetize the throat and mouth areas, thereby providing relief to irritated areas. Increased availability of the anesthetic is possible by the formation of a sweetener-/anesthetic premix. The preferred anesthetic is hexylresourcinol.

11 Claims, No Drawings

ANESTHETIC-CONTAINING CHEWING GUM COMPOSITIONS

This invention relates to chewing gum compositions capable of providing an anesthetic effect to the mouth and throat areas. More particularly, the compositions of this invention contain an anesthetic-producing active. Due to the high amount of the anesthetic released, these compositions are particularly useful as sore throat remedies.

To produce an effective sore throat chewing gum composition it is necessary that the anesthetic be released in sufficient amounts to provide a numbing effect in the inflamed or irritated mouth and throat areas. It is a well known phenomenon that a predominate portion of the chewing gum composition, i.e. particularly the flavors and ingredients associated therewith, becomes entrapped in the gum base bolus during mastication. Thus, this concern is also present when actives such as anesthetics are added directly to the gum base. Entrapment of the active in the bolus results in less contact of the active with the mouth and throat areas and a resultant failure to provide effective numbing to the painful areas.

The art has disclosed anesthetics such as hexylresourcinol in lozenge form such that the active is released as the lozenge slowly dissolves in the mouth. The art has not, however, disclosed a chewing gum composition which is pleasing to taste, yet designed to provide sufficient release of the anesthetic to effectuate numbing.

It has been discovered that when the anesthetic is premixed with a material which is readily released during mastication, such as a sweetener, and added to the chewing gum composition, the percentage of the anesthetic released upon chewing is increased over simple addition of the active independent of the sweetener. Additionally, the bitter taste of many anesthetics is greatly mitigated due to its intimate contact with the sweetener, which effectively masks the anesthetic's initial off-taste. Once the inventive compositions are chewed for a few minutes, the anesthetic is released in sufficient amounts to begin numbing the throat and mouth area such that taste of the anesthetic is no longer a concern. The increase in release of anesthetic over prior art formulations results, however, in a chewing gum composition having greater anesthetic effect. Thus, chewing gums designed as sore throat remedies can now be prepared, giving the consumer an alternative to lozenges, which heretofore where the best method of insuring adequate release of the anesthetic and subsequent relief to the consumer.

Accordingly, the instant invention concerns a chewing gum composition and method of preparing same, said composition being capable of providing an anesthetic effect to the throat and mouth areas through the release of an anesthetic, comprising:
(a) about 16 to about 30% gum base;
(b) about 0.5 to about 3% flavor; and
(c) a premixture of sweetener and anesthetic, said premixture comprising about 50 to about 80% sweetener and a sufficient amount of anesthetic to provide an anesthetic effect to the mouth and throat areas.

Useful anesthetics may be selected from the group generally known as local or topical anesthetics. Preferably the anesthetic is selected from the group consisting of hexylresourcinol, benzocaine, xylocaine, lidocaine, tetracaine, tripelennamine, dibucane, sodium phenolate, chloroprocaine, etidocaine, bupivacaine and mixtures thereof. Pharmaceutically acceptable salts and equivalent derivatives of these compounds are contemplated. The amount of anesthetic present is preferably in the range of about 0.05 to about 0.5%. It is preferred that each gum piece made from the inventive composition contain about 1.5 to about 5.0 mg of anesthetic and preferably about 2 to about 2.4 mg per gum piece.

The process for preparing chewing gum compositions capable of producing anesthetic effects concerns the addition of the premixed sugar/anesthetic to the chewing gum portion of the total compositions, rather than the addition of sweetener and anesthetic as separate, individual components. More particularly, the process comprises the steps of:

(1) providing a gum base comprising elastomers, softeners and optionally corn syrup;
(2) forming a premix comprising sweetener particles in the amount of about 50 to about 80% and an anesthetic-producing active in amounts of up to about 0.5%, all amounts based on the total gum composition;
(3) adding the premix of (b) to the gum base of (a);
(4) adding additional conventional ingredients selected from the group consisting of flavorings, softeners, emulsifiers, coloring, plasticizers, and mixtures thereof and mixing to obtain a homogeneous mass; and
(5) forming chewing gum pieces therefrom.

The present invention allows for relatively low levels of anesthetic to be present since the problem of base entrapment of the anesthetic is significantly less, thereby making the anesthetic more available for release.

The instant invention is designed to specifically allow and facilitate simultaneous release of the sugar or other sweetener with the anesthetic. It was discovered that simple addition of the individual components of sweetener and anesthetic into the chewing gum portion of the chewing gum composition would not yield simultaneous release for the simple reason that they would not be physically bound together and would therefore release at different rates. Additionally, the anesthetic tends to become entrapped in the gum base unless it is carried out into the saliva by the sweetener. Attempts to admix anesthetics such as hexylresourcinol with flavor as a means of producing greater release have not been entirely successful and result in the anesthetic becoming entrapped in the gum base bolus.

In preparing the formulation for use in the instant process, a portion of or all of the sweeteners and bulking agents traditionally added to the gum base portion of the chewing gum composition may be mixed with the gum base prior to the addition of the premix. The gum base thus becomes saturated and bound by the sweeteners and bulking agents and will be unlikely to absorb the premix. In this manner, migration of the premix into the gum base will be precluded, thereby preventing the premix components from becoming locked into the gum base.

The anesthetic may be encapsulated or partially entrapped prior to incorporation to the premix. Materials which are microporous are best suited for use as the encapsulant since they do not impede the ultimate release of the anesthetic, but control the speed to some extent. Thus, for example, to achieve a sustained release effect, some of the anesthetic may be entrapped in a microporous material such as maltodextrin, and then added to the sweetener to form the premix. The bulk density of the maltodextrin best suited for this purpose is in the range of about 3.0 to about 6.0 lbs./cu. ft. Other suitable encapsulating materials are contemplated.

The gum base used in this invention may be any water-insoluble gum base well known in the art. Illustrative examples of suitable polymers in gum bases include both natural and synthetic elastomers and rubbers. For example, those polymers which are suitable in gum bases, include, without limitation, substances or vegetable origin such as chicle, jelutong, balata, gutta percha, lechi caspi, sorva, guayale rubber, crown gum and mixtures thereof. Synthetic elastomers such as butadiene-styrene copolymers, isobutylene-isoprene copolymers, polyethylene, polyisobutylene, polyvinylacetate and mixtures thereof, are particularly useful.

The amount of gum base employed will vary greatly depending on various factors such as the type of base used, consistency desired and other components used to make the final product. In general, amounts of about 5% to about 45% by weight of the final chewing gum composition are acceptable for use in chewing gum compositions with preferred amounts of about 16% to about 30% by weight. The most preferred range is about 19 to about 28% by weight.

The gum base composition may contain elastomer solvents to aid in softening the rubber component. Such elastomer solvents may comprise methyl, glycerol or pentaerythritol esters of rosins or modified rosins, such as hydrogenated, dimerized or polymerized rosins or mixtures thereof. Examples of elastomer solvents suitable for use herein include the pentaerythritol ester of partially hydrogenated wood rosin, pentaerythritol ester of wood rosin, glycerol ester of wood rosin, glycerol ester of partially dimerized rosin, glycerol ester of polymerized rosin, glycerol ester of tall oil rosin, glycerol ester of wood rosin and partially hydrogenated wood rosin and partially hydrogenated methyl ester of rosin, such as polymers of alpha-pinene or beta-pinene; terpene resins including polyterpene and mixtures thereof. The solvent may be employed in an amount ranging from about 10% to about 75% and preferably about 45% to about 70% by weight to the gum base.

A variety of traditional ingredients such as plasticizers or softeners such as lanolin, stearic acid, sodium stearate, potassium stearate, glyceryl triacetate, glycerine and the like for example, natural waxes, petroleum waxes, such as polyurethane waxes, paraffin waxes and microcrystalline waxes may also be incorporated into the gum base to obtain a variety of desirable textures and consistency properties. These individual additional materials are generally employed in amounts of up to about 30% by weight and preferably in amounts of from about 3% to about 20% by weight of the final gum base composition.

The chewing gum composition may additionally include the conventional additives of flavoring agents; coloring agents such as titanium dioxide; emulsifiers such as lecithin and glyceryl monostearate; and additional fillers such as aluminum hydroxide, alumina, aluminum silicates, calcium carbonate, and talc and combinations thereof. These fillers may also be used in the gum base in various amounts. Generally, fillers are used in amounts of up to about 30%. Preferably the amount of fillers when used will vary from about 4% to about 10% by weight of the final chewing gum.

The present invention contemplates the inclusion of those sweeteners well known in the art, including both natural and artificial sweeteners. Thus, sweeteners may be chosen from the following non-limiting list: sugars such as sucrose, glucose (corn syrup), dextrose, invert sugar, fructose, and mixtures thereof; saccharine and its various salts such as the sodium or calcium salt; cyclamic acid and its various salts such as the sodium salt; amino acid-based and dipeptide sweeteners such as aspartame; dihydrochalcone compounds; talin; sucralose; glycyrrhizin; *Stevia Rebaudiana* (Stevioside); and sugar alcohols such as sorbitol, sorbitol syrup, mannitol, xylitol, and the like. Also contemplated as an additional sweetener is the nonfermentable sugar substitute (hydrogenated starch hydrolysate) which is described in U.S. Pat. No. Re. 26,959. Also contemplated is the synthetic sweetener 3,6-dihydro-6-methyl-1-1,2,3-oxathiazin-4-one-2,2-dioxide particularly the potassium (Acesulfame-K), sodium and calcium salts thereof as described in German patent No. 2,001,017.7.

In general, the amount of sweetener will vary with the desired amount of sweeteners selected for a particular chewing gum. This amount will normally be 0.001% to about 60% by weight when using an easily extractable sweetener. The water-soluble sweeteners described in category A above, are preferably used in amounts of about 25% to about 60% by weight. In contrast, the artificial sweetener described in categories B and C are used in amounts of about 0.005% to about 5.0% and most preferably about 0.05% to about 2.5% by weight of the final gum composition These amounts are ordinarily necessary to achieve a desired level of sweetness independent from the flavor level achieved from flavor oils.

Flavoring agents well known to the chewing gum art may be added to the chewing gum compositions of the instant invention. Suitable flavorings include both natural and artificial flavors, and mints such as peppermint and spearmint; menthol; oil of wintergreen; artificial vanilla; cinnamon; kola flavor and kola extract; citrus flavors such as orange, lemon and lime; fruit flavors such as banana, apple, pear, blueberry, strawberry, cherry and grape. Flavorings can be used alone or in combination with each other to achieve the desired effect and taste. The flavorings are generally utilized in amounts that will vary depending upon the individual flavor, and may, for example, range in amounts of about 0.5% to about 3% by weight of the final chewing gum composition weight.

Of particular importance is a unique flavor combination, which due to the characteristics of the individual constituents, produces an anesthetic effect independent of the anesthetic active. This flavor combination, when added to a chewing gum alone is perceived as producing a significantly greater numbing effect than the use of any of the flavor ingredients individually. When added to the preferred inventive compositions containing hexylresourcinol, the anesthetic impact was increased while simultaneously delivering the cooling effect inherent to the mint oils and menthol. The flavor combination comprises mint oil (peppermint or spearmint), menthol, ginger oil and clove oil in admixture such that their total combined weight added to the chewing gum composition is up to about 2%. This combination is generally premixed prior to incorporation in the chewing gum composition.

The colorants useful in the present invention include the pigments such as titanium dioxide, that may be incorporated in amounts of up to about 1% by weight, and preferably up to about 0.6% by weight. Also, the colorants may include other dyes suitable for food, drug and cosmetic applications, and known as F.D. & C. dyes and the like. The materials acceptable for the foregoing spectrum of use are preferably water-soluble. Illustrative examples include indigoid dye, known as F.D. & C. Blue No. 2, which is the disodium salt of 5,5'-indigotindisulfonic acid. Similarly, the dye known as F.D. & C. Green No. 1, comprises a triphenylmethane dye and is the monosodium salts of 4-[4-Methyl- p-sulfobenzylamino)diphenylmethylene]-[1-(N-ethyl-N-p-sulfoniumbenzyl)- 2,5-cyclohexadienimine]. A full recitation of all F.D. & C. and D. & C. and their corresponding chemical structures may be found in the Kirk-Othmer Encyclopedia of Chemical Technology, in Volume 5, at Pages 857–884, which text is accordingly incorporated herein by reference.

The inventive compositions can be used to prepare sugar or sugarless chewing gums and may be substantially anhydrous as well. Regular and non-adhering (non-stick) formulations are contemplated. Bubble gum, stick gum, pillow shaped, chunk, coated and other gum piece forms well known to the art are contemplated.

The inventive formulations have been found to be an effective device for those requiring a substitute for smoking.

The following examples are given to illustrate the invention, but are not deemed to be limiting thereof. All percentages given throughout the specification are based upon weight of the total chewing gum composition unless otherwise indicated.

EXAMPLES

Chewing gum compositions were prepared in accordance with the instant invention using the formulations set forth in the table below. Compositions have the prefix "I" represent those of the invention and compositions with the prefix "C" represent compositions of the prior art (controls). The inventive compositions used a sweetener/hexylresourcinol premix. Both sugar and sugarless versions are shown.

All of the prior art compositions except C-1 had hexylresourcinol added separately from the sugar. C-1 had a premix of flavor/hexylresourcinol.

Chewing gum pieces were prepared from each of the compositions and chewed by an expert panel for 30 minutes. The gum bolus was then assayed for the percentage of hexylresourcinol remaining after chew. From this information, the percentage of hexylresourcinol released was calculated. The inventive compositions (I-1 through I-4) showed that from 48% to 63% of the hexylresourcinol was released, i.e., chewed out. These chewing gums also produced a strong anesthetic effect in the throat and mouth area of the expert panelists. The prior art compositions, however, exhibited little or no effective release of the hexylresourcinol as perceived by the panelists, as indicated by the lack of anesthetic effect on the mouth and throat region.

The invention being thus described, it will be obvious that the same may be varied in many ways. Such variations are not to be regarded as a departure from the spirit and scope of the invention and all such modifications are intended to be included within the scope of the claims.

| | CHEWING GUM COMPOSITIONS % BY WEIGHT | | | | | | | | |
|---|---|---|---|---|---|---|---|---|---|
| INGREDIENT | I-1 | I-2 | I-3 | I-4 | C-1 | C-2 | C-3 | C-4 | C-5 |
| Gum Base | 28 | 26 | 26 | 26 | 19 | 28 | 26 | 28 | 26 | 21 |
| Emulsifier | 0.5 | 0.5 | 0.5 | 0.5 | 0.5 | 0.5 | 0.5 | 0.5 | 0.5 |
| Premix | | | | | | | | | |
| Sugar/HR[1] | 63/0.12 | — | — | 70.18/0.075 | — | — | — | — | — |
| Mannitol/HR | — | 7/0.12 | — | — | — | — | — | — | — |
| Flavor/HR | — | — | — | — | 17.3/0.12 | — | — | — | — |
| Flavor/Mannitol/HR | — | — | 7/0.12 | — | — | — | — | — | — |
| Flavor | 1.73 | 1.78 | 1.78 | 1.1 | — | 1.78 | 1.93 | 1.78 | 1.1 |
| Sorbitol | — | 48.34 | 48.34 | — | — | — | — | 48.34 | — |
| Mannitol | — | — | — | — | — | — | — | 7.0 | — |
| Sugar | — | — | — | — | 61.0 | 62.95 | 60.8 | — | 68.65 |
| Menthol | 1.15 | 1.34 | 1.34 | 1.15 | 1.15 | 1.15 | 1.15 | 1.34 | — |
| Humectant | 5.0 | 13.5 | 13.5 | 4.0 | 5.0 | 5.0 | 5.0 | 13.5 | 4.0 |
| Maltodextrin | 2.5 | — | — | 4.0 | 2.5 | 2.5 | 2.5 | — | 4.0 |
| Aspartame Encapsulated[2] | — | 1.42 | 1.42 | — | — | — | — | 1.42 | — |
| Free Hexylresourcinol | — | — | — | — | — | 0.12 | 0.12 | 0.12 | 0.75 |
| % Hexylresourcinol released during 30 minute chewout panel | 63% | 53% | 57% | 48% | — | — | — | — | — |

[1]HR indicates hexylresourcinol anesthetic.
[2]Represents 0.384% aspartame, 1.036% hydrophobic encapsulant.

We claim:

1. A palatable chewing gum composition capable of providing an anesthetic effect to the mouth and throat areas through the simultaneous release of a local anesthetic and a sweetener, said composition by weight of total composition, consisting essentially of:
   (a) about 16 to about 30% gum base;
   (b) about 0.5% to about 3% flavor; and
   (c) a premixture of sweetener and anesthetic, said premixture comprising about 50 to about 80% sweetener admixed with an anesthetic in an amount of from about 0.05 to about 0.5% by weight of the total gum composition which is sufficient to produce an anesthetic effect in the mouth and throat areas upon chewing of the composition.

2. The chewing gum composition of claim 1 wherein the composition is capable of releasing up to about 80% of the anesthetic present.

3. The chewing gum composition of claim 1 wherein the anesthetic is in the encapsulated or entrapped form.

4. The chewing gum composition of claim 3 wherein the encapsulating material is microporous maltodextrin having a bulk density of about 3.0 to about 6.0 lbs./cu. ft.

5. The chewing gum composition of claim 1, wherein the anesthetic is selected from the group consisting of hexylresourcinol, benzocaine, xylocaine, lidocaine, tetracine, tripelennamine, dibucane, sodium phenoloate, bupivacaine, chloroprocaine, etidocaine and mixtures and pharmaceutically acceptable salts thereof.

6. The chewing gum composition of claim 1 wherein the gum base is selected from the group consisting of synthetic gums, natural gums, synthetic elastomers, natural elastomers and mixtures thereof.

7. The composition of claim 1 wherein the sweetener is selected from the group consisting of water-soluble natural sweeteners, water-soluble artificial sweeteners, dipeptide sweeteners, amino acid-based sweeteners and mixtures thereof.

8. The composition of claim 7 wherein the sweetener is selected from the group consisting of sucrose, fructose, glucose (corn syrup), dextrose, invert sugar; saccharine and its salts; cyclamic acid and its salts; aspartame; dihydrochalcone; glycyrrhizin; Stavia Rebaudiana (stevioside); sorbitol, mannitol, xylitol; hydrogenated starch hydrolysate; 3,6-dihydro-6-methyl-1-1,2,3-oxathiazin-4-one-2,2-dioxide (acesulfame-) and its salts; talin; sucralose; and combinations thereof.

9. The composition of claim 1 wherein the flavor is selected from the group consisting of natural flavors, artificial flavors and mixtures thereof.

10. The composition of claim 9 wherein the flavor is selected from the group consisting of peppermint oil, spearmint oil, methol, clove, ginger, cinnamon oil, oil of wintergreen, fruit flavors and essences, kola flavor, kola extract and combinations thereof.

11. A method of preparing a palatable chewing gum composition capable of releasing anesthetic-producing active in amounts sufficient to produce an anesthetic effect in the mouth and throat area, consisting essentially of the following steps:
 (1) providing a gum base comprising elastomers, softeners;
 (2) forming a premix comprising sweetener particles in the amount of about 50 to about 80% admixed with an anesthetic in an amount of from about 0.05% to about 0.5% by weight of the total gum composition which is sufficient to produce an anesthetic effect;
 (3) adding the premix of (b) to the gum base of (a);
 (4) adding additional conventional ingredients selected from the group consisting of flavorings, softeners, emulsifiers, coloring, plasticizers, and mixtures thereof and mixing to obtain a homogeneous mass; and
 (5) forming chewing gum pieces therefrom.

* * * * *